United States Patent
Oestdal et al.

(10) Patent No.: US 11,051,520 B2
(45) Date of Patent: Jul. 6, 2021

(54) LIPOLYTIC ENZYME FOR USE IN BAKING

(71) Applicants: Novozymes A/S, Bagsvaerd (DK); Puratos NV/SA, Groot-Bijgaarden (BE)

(72) Inventors: Henrik Oestdal, Virum (DK); Sara Maria Landvik, Vedbaek (DK); Robert Piotr Olinski, Vaerloese (DK); Evelien Agache, Drongen (BE); Bruno Van Winckel, Ghent (BE); Filip Arnaut, Rosdaal (BE)

(73) Assignees: Novozymes A/S, Bagsvaerd (DK); Puratos NV/SA, Groot-Bijgaarden (BE)

(*) Notice: Subject to any disclaimer, the term of this patent is extended or adjusted under 35 U.S.C. 154(b) by 0 days.

(21) Appl. No.: 16/485,749

(22) PCT Filed: Feb. 19, 2018

(86) PCT No.: PCT/EP2018/054015
§ 371 (c)(1),
(2) Date: Aug. 13, 2019

(87) PCT Pub. No.: WO2018/150021
PCT Pub. Date: Aug. 23, 2018

(65) Prior Publication Data
US 2019/0364912 A1    Dec. 5, 2019

(30) Foreign Application Priority Data
Feb. 20, 2017 (EP) .................................... 17156925

(51) Int. Cl.
| A21D 2/26 | (2006.01) |
| C12N 9/20 | (2006.01) |
| A21D 8/04 | (2006.01) |
| A21D 10/00 | (2006.01) |

(52) U.S. Cl.
CPC ............ *A21D 8/042* (2013.01); *A21D 10/002* (2013.01); *C12N 9/20* (2013.01); *C12Y 301/01003* (2013.01)

(58) Field of Classification Search
None
See application file for complete search history.

(56) References Cited

U.S. PATENT DOCUMENTS

| 6,110,508 | A | 8/2000 | Olesen et al. |
| 6,140,094 | A | 10/2000 | Loffler et al. |
| 2007/0166432 | A1* | 7/2007 | Liu ........................ A21D 8/042 426/20 |
| 2008/0118965 | A1 | 5/2008 | Andries |
| 2010/0192985 | A1* | 8/2010 | Aehle ................ C11D 3/38645 134/26 |
| 2011/0091601 | A1 | 4/2011 | Borch et al. |
| 2013/0122144 | A1 | 5/2013 | Tsukazaki |

FOREIGN PATENT DOCUMENTS

| WO | 1998/26057 A1 | 6/1998 |
| WO | 1999/053769 A1 | 10/1999 |
| WO | 2002/094123 A2 | 11/2002 |
| WO | 2004/099400 A2 | 11/2004 |
| WO | 2014/147219 A1 | 9/2014 |

* cited by examiner

*Primary Examiner* — David Steadman
(74) *Attorney, Agent, or Firm* — Elias Lambiris

(57) ABSTRACT

A polypeptide having lipolytic enzyme activity, selected from the group consisting of: (a) a polypeptide having at least 65% sequence identity to amino acids 21 to 309 of SEQ ID NO: 1; (b) a polypeptide encoded by a polynucleotide that hybridizes under medium stringency conditions with the polypeptide coding sequence of SEQ ID NO: 2; (c) a polypeptide encoded by a polynucleotide having at least 65% sequence identity to the polypeptide coding sequence of SEQ ID NO: 2; and (d) a fragment of the polypeptide of (a), (b) or (c) that has lipolytic enzyme activity.

20 Claims, No Drawings
Specification includes a Sequence Listing.

LIPOLYTIC ENZYME FOR USE IN BAKING

CROSS-REFERENCE TO RELATED APPLICATIONS

This application is a 35 U.S.C. 371 national application of international application no. PCT/EP2018/054015 filed Feb. 19, 2018 and published on Aug. 23, 2018 as WO 2018/150021, which claims priority or the benefit under 35 U.S.C. 119 of European application no. 17156925.4 filed Feb. 20, 2017, the contents of which are fully incorporated herein by reference.

REFERENCE TO AN ELECTRONIC SEQUENCE LISTING

This application contains an electronic Sequence Listing in computer readable form. The electronic sequence listing (name: 14303-WO-PCT SQ listing.txt; size: 16,107 bytes; date of creation: Feb. 19, 2018) is incorporated herein by reference in its entirety.

FIELD OF INVENTION

The present invention relates to new lipolytic enzymes; especially to lipolytic enzymes with improved properties for use in dough, where they, e.g., may substitute emulsifiers normally used in baking.

BACKGROUND OF THE INVENTION

White crumb and a fine crumb structure are important features for consumer preference of bread; especially of industrially packed bread such as toast bread. A fine crumb structure is normally achieved by adding an emulsifier to the dough during bread making.

Nowadays, consumers tend to avoid consuming bakery products that contain emulsifiers.

The use of lipolytic enzymes in baking has been known for many years.

WO 98/26057 discloses a lipase/phospholipase from *Fusarium oxysporum* and its use in baking.

WO 2004/099400 discloses various lipolytic enzymes and their use in baking for reduction of dough stickiness.

WO 1999/053769 discloses the use of maltogenic alpha-amylase and phospholipase for improved softness of the baked product in the initial period after baking.

The use of lipolytic enzymes in baking may provide an unwanted off-flavor due to formation of free chain fatty acids.

The present invention refers to new lipolytic enzymes capable of providing a white crumb and a fine crumb structure without inducing off-flavor.

SUMMARY OF THE INVENTION

The inventors have found a new lipolytic enzyme which surprisingly provides a white crumb and a very fine crumb structure, and at the same time the lipolytic enzyme does not provide off-flavor when used in baking, so we claim:

A polypeptide having lipolytic enzyme activity, selected from the group consisting of:

(a) a polypeptide having at least 65% sequence identity to amino acids 21 to 309 of SEQ ID NO: 1;

(b) a polypeptide encoded by a polynucleotide that hybridizes under medium stringency conditions with the polypeptide coding sequence of SEQ ID NO: 2;

(c) a polypeptide encoded by a polynucleotide having at least 65% sequence identity to the polypeptide coding sequence of SEQ ID NO: 2; and (d) a fragment of the polypeptide of (a), (b) or (c) that has lipolytic enzyme activity.

In one embodiment, the lipolytic enzyme according to the invention has at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the to amino acids 21 to 309 of SEQ ID NO: 1.

In one embodiment, the lipolytic enzyme according to the invention comprises a catalytic segment of the amino acid sequence G-H-S-L-G (SEQ ID NO: 5).

In one embodiment, the lipolytic enzyme according to the invention has lipase, phospholipase and/or galactolipase activity; especially the lipolytic enzyme has lipase and phospholipase activity.

In one embodiment, we claim an isolated polynucleotide encoding the lipolytic enzyme according to the invention.

In one embodiment, we claim a nucleic acid construct or expression vector comprising the polynucleotide encoding the lipolytic enzyme according to the invention operably linked to one or more control sequences that direct the production of the polypeptide in an expression host.

In one embodiment, we claim a recombinant host cell comprising the polynucleotide encoding the lipolytic enzyme according to the invention operably linked to one or more control sequences that direct the production of the polypeptide.

In one embodiment, we claim a method of producing the lipolytic enzyme according to the invention comprising cultivating a host cell under conditions conducive for production of the polypeptide.

In one embodiment, we claim a granulate or a stabilized liquid comprising the lipolytic enzyme according to the invention.

In one embodiment, we claim a composition comprising the lipolytic enzyme according to the invention and one or more enzymes selected from the group consisting of aminopeptidase, amylase, alpha-amylase, maltogenic alpha-amylase, beta-amylase, carboxypeptidase, catalase, chitinase, cutinase, cyclodextrin glycosyltransferase, deoxyribonuclease, esterase, galactanase, glucan 1,4-alpha-maltotetrahydrolase, glucanase, alpha-galactosidase, beta-galactosidase, glucoamylase, alpha-glucosidase, beta-glucosidase, haloperoxidase, invertase, laccase, mannanase, mannosidase, oxidase, pectinolytic enzymes, peptidoglutaminase, peroxidase, phospholipase, phytase, polyphenoloxidase, proteolytic enzyme, ribonuclease, transglutaminase, and xylanase; in particular a composition comprising the lipolytic enzyme according to the invention and one or more enzymes selected from the group consisting of maltogenic alpha-amylase, beta-amylase and glucan 1,4-alpha-maltotetrahydrolase; especially a composition comprising the lipolytic enzyme according to the invention and a maltogenic alpha-amylase.

In one embodiment, we claim a method for preparing a baked product, comprising the step of adding to the dough, prior to baking, a lipolytic enzyme according to the invention, a granulate or a stabilized liquid according to the invention, or a composition according to the invention.

In one embodiment, the amount of lipolytic enzyme according to the invention is between 0.01 and 100 mg, preferably between 0.05 and 50 mg, more preferably between 0.1 and 25 mg, even more preferably between 0.1 and 15 mg enzyme protein per kg flour in the dough or in the batter.

In one embodiment, we claim the use of a lipolytic enzyme according to the invention in bakery and/or patisserie applications.

In one embodiment, we claim the use of a granulate or a stabilized liquid comprising the lipolytic enzyme according to the invention in bakery and/or patisserie applications.

In one embodiment, we claim the use of a composition comprising the lipolytic enzyme according to the invention and one or more additional enzymes in bakery and patisserie applications.

In one embodiment, we claim the use of the lipolytic enzyme according to the invention in bread improvers and/or in patisserie mixes or premixes.

DETAILED DESCRIPTION OF THE INVENTION

Definitions

Lipolytic enzyme: The term "a lipolytic enzyme" comprises an enzyme (EC 3.1.1) having lipase, phospholipase and/or galactolipase activity; especially an enzyme having lipase and phospholipase activity. The lipolytic enzyme may also have other activities. The term "lipolytic enzyme" is used interchangeably with the term "polypeptides having lipolytic enzyme activity".

According to the present invention, lipase activity may be measured by the following method:

The lipase activity may be determined using tributyrine as substrate. This method is based on the hydrolysis of tributyrin by the enzyme, and the alkali consumption to keep pH constant during hydrolysis is registered as a function of time.

One Lipase Unit (LU) is defined as the amount of enzyme which, under standard conditions (i.e., at 30° C.; pH 7.0; with 0.1% w/v Gum Arabic as emulsifier and 0.16 M tributyrine as substrate) liberates 1 micro mole titratable butyric acid per minute.

A useful protocol for identifying lipase activity is the following using tributyrin plates:
Tributyrin Substrate Mix:
15 ml Glycerintributyrate (tributyrin)
2 g gum Arabic.
285 ml $H_2O$
For 2 plates use:
  5 ml tributyrin mix, add 50 ml 0.02 M Universal buffer at pH 7.0
  Pre-warm to 60° C.
  Ultra turax for 60 seconds to get a smooth emulsion
Make a 2% Agarose Solution:
  2 g for 100 ml $H_2O$
  Boil and bring the solution to 60° C. (use a water bath)
Mix 50 ml tributyrin/buffer solution with 50 ml 2% agarose, add 250 micro liter 4% Crystal violet. Pour 50 ml for each plate OmniTray Single Well cat no 242811, and Nunc TSP 96 Cat no 445497. 10 microliter samples may be applied. The plates may be incubated at 30° C. for approx. 1 hour and 3 hours. The activity may be photographed.

Lipase activity: Triacylglycerol lipase activity (EC 3.1.1.3), i.e., hydrolytic activity for carboxylic ester bonds in triglycerides, e.g., tributyrin.

Phospholipase activity: Phospholipase activity (A1 or A2, EC 3.1.1.32 or 3.1.1.4), i.e., hydrolytic activity towards one or both carboxylic ester bonds in phospholipids such as lecithin.

Galactolipase activity: Galactolipase activity (EC 3.1.1.26), i.e., hydrolytic activity on carboxylic ester bonds in galactolipids such as DGDG (digalactosyl diglyceride).

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Fragment: The term "fragment" means a polypeptide having one or more (e.g., several) amino acids absent from the amino and/or carboxyl terminus of a mature polypeptide or domain; wherein the fragment has lipolytic enzyme activity.

Host cell: The term "host cell" means any cell type that is susceptible to transformation, transfection, transduction, or the like with a nucleic acid construct or expression vector comprising a polynucleotide of the present invention.

Isolated: The term "isolated" means a substance in a form or environment that does not occur in nature. Non-limiting examples of isolated substances include (1) any non-naturally occurring substance, (2) any substance including, but not limited to, any enzyme, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc.

Mature polypeptide coding sequence: The term "mature polypeptide coding sequence" means a polynucleotide that encodes a mature polypeptide having lipolytic enzyme activity.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times—each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times—each for 15 minutes using 2×SSC, 0.2% SDS at 60° C.

High stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Sequence identity: The relatedness between two amino acid sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment).

A polypeptide having lipolytic enzyme activity according to the invention may comprise an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment).

Improved property: When incorporated into dough in effective amounts, the lipolytic enzyme according to the invention may improve one or more properties of the dough or of the baked product obtained therefrom.

The term "improved property" is defined herein as any property of dough and/or a product obtained from the dough, particularly a baked product, which is improved by the action of the lipolytic enzyme according to the invention relative to dough or the product obtained from the dough in which the lipolytic enzyme according to the invention is not incorporated.

The improved property may include, but is not limited to, improved whiteness of the crumb of the baked product, improved crumb structure of the baked product, improved crumb softness of the baked product, improved flavor of the baked product, and/or improved anti-staling properties of the baked product.

The improved property may be determined by comparison of doughs and/or a baked products prepared with and without addition of the lipolytic enzyme according to the invention.

Organoleptic qualities may be evaluated using procedures well established in the baking industry, and may include, for example, the use of a sensory panel.

Improved crumb structure of the baked product: The term "improved crumb structure of the baked product" is defined herein as a baked product with a finer crumb. Improved crumb fineness is associated with smaller cells and/or thinner cell walls in the crumb and/or more uniform/homogenous distribution of cells in the crumb, and is usually evaluated visually by the baker/sensory panel, or by digital image analysis as known in the art (e.g., C-cell, Calibre Control International Ltd, Warrington, UK, as shown in Examples 2-3 of the present invention).

Improved whiteness of the crumb: Crumb fineness is often evaluated by measuring whiteness of the bread crumb, because finer crumb structure reflects the light in a manner making the crumb appear more white. The whiteness of the crumb may be measured as known in the art, e.g., by using the HunterLab L-value measured with a color scanner.

Improved crumb softness of the baked product: The term "improved crumb softness of the baked product" is the opposite of "firmness" and is defined herein as the property of a baked product that is more easily compressed and is evaluated either empirically by the skilled test baker/sensory panel or measured by the use of a texture analyzer (e.g., TAXT2 or TA-XT Plus from Stable Micro Systems Ltd, Surrey, UK) as known in the art.

Improved flavor of the baked product: The term "improved flavor of the baked product" is evaluated by a trained test panel and/or chemical analysis (e.g., headspace GC-MS analysis). Improved flavor of the baked product comprises the reduction of off-flavor(s) of the baked product.

Improved anti-staling of the baked product: The term "improved anti-staling of the baked product" is defined herein as the properties of a baked product that have a reduced rate of deterioration of quality parameters, e.g., softness and/or elasticity, during storage.

Volume of the baked product: The term "volume of the baked product" is measured as the volume of a given loaf of bread. The volume may be determined by the rape seed displacement method.

Off-flavor: The term whether or not a baked product has off-flavor is evaluated by a trained test panel/chemical analysis as known in the art.

Lipolytic Enzymes According to the Invention

Lipolytic enzymes which are suitable for use in the present invention include a polypeptide having lipolytic enzyme activity, selected from the group consisting of:

(a) a polypeptide having at least 65% sequence identity to amino acids 21 to 309 of SEQ ID NO: 1;

(b) a polypeptide encoded by a polynucleotide that hybridizes under medium stringency conditions with the polypeptide coding sequence of SEQ ID NO: 2;

(c) a polypeptide encoded by a polynucleotide having at least 65% sequence identity to the polypeptide coding sequence of SEQ ID NO: 2; and (d) a fragment of the polypeptide of (a), (b) or (c) that has lipolytic enzyme activity.

For purposes of the present invention, the mature polypeptide disclosed in SEQ ID NO: 1 is used to determine the corresponding amino acid residue in another lipolytic enzyme.

The amino acid sequence of another lipolytic enzyme is aligned with the mature polypeptide disclosed in SEQ ID NO: 1, and based on the alignment, the amino acid position number corresponding to any amino acid residue in the mature polypeptide disclosed in SEQ ID NO: 1 is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix.

In one embodiment, the lipolytic enzyme according to the invention has at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the amino acids 21 to 309 of SEQ ID NO: 1.

In one embodiment, the lipolytic enzyme according to the invention comprises a catalytic triad of the amino acid sequence G-H-S-L-G (SEQ ID NO: 5).

A lipolytic enzyme of the present invention preferably comprises or consists of the amino acids 21 to 309 of SEQ ID NO: 1; or is an allelic variant thereof; or is a fragment thereof having lipolytic enzyme activity.

In another embodiment, the present invention relates to an isolated polypeptide having lipolytic enzyme activity encoded by a polynucleotide that hybridizes under very low stringency conditions, low stringency conditions, medium stringency conditions, medium-high stringency conditions, high stringency conditions, or very high stringency conditions with the mature polypeptide coding sequence of SEQ ID NO: 2, (Sambrook et al., 1989, *Molecular Cloning, A Laboratory Manual*, 2d edition, Cold Spring Harbor, N.Y.).

The polynucleotide of SEQ ID NO: 2 or a subsequence thereof, as well as the polypeptide of SEQ ID NO: 1 or a fragment thereof, may be used to design nucleic acid probes to identify and clone DNA encoding polypeptides having lipolytic enzyme activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having lipolytic enzyme activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 2 or a subsequence thereof, the carrier material may be used in a Southern blot.

For purposes of the present invention, hybridization indicates that the polynucleotide hybridizes to a labeled nucleic acid probe corresponding to (i) SEQ ID NO: 2; (ii) the mature polypeptide coding sequence of SEQ ID NO: 2; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In another embodiment, the present invention relates to an isolated polypeptide having lipolytic enzyme activity encoded by a polynucleotide having a sequence identity to the mature polypeptide coding sequence of SEQ ID NO: 2 of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 1 comprising a substitution, deletion, and/or insertion at one or more (e.g., several) positions. In an embodiment, the number of amino acid substitutions, deletions and/or insertions introduced into the mature polypeptide of SEQ ID NO: 1 is not more than 20, e.g., 1, 2, 3, 4, 5, 6, 7, 8, 9, 10, 11, 12, 13, 14, 15, 16, 17, 18, or 19. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for lipolytic enzyme activity to identify amino acid residues that are critical to the activity of the molecule. See also, Hilton et al., 1996, *J. Biol. Chem.* 271: 4699-4708.

The active site of the enzyme or other biological interaction can also be determined by physical analysis of structure, as determined by such techniques as nuclear magnetic resonance, crystallography, electron diffraction, or photo-affinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus to a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Lipolytic Enzyme Activity

A polypeptide having lipolytic enzyme activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one aspect, the polypeptide is obtained from *Valsaria*, such as, but not limited to, *Valsaria rubricosa*.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art.

Polynucleotides

The present invention also relates to isolated polynucleotides encoding a polypeptide, of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Valsaria*, e.g., *Valsaria rubricosa*, or a related organism.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermos-stability, pH optimum, or the like. The variants may be constructed on the basis of the polynucleotide presented as the mature polypeptide coding sequence of SEQ ID NO: 2, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulaturn, Fusarium roseum, Fusarium sambucinum, Fusarium sarcochroum, Fusarium sporotrichioides, Fusarium sulphureum, Fusarium torulosum, Fusarium trichothecioides, Fusarium venenaturn, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell; in particular an *Aspergillus oryzae* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for lipolytic enzymes. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Compositions Comprising a Lipolytic Enzyme According to the Invention

The present invention relates to compositions comprising the lipolytic enzyme according to the invention.

The composition may further comprise one or more additional enzymes, in particular one or more enzymes selected from the group consisting of aminopeptidase, amylase, alpha-amylase, maltogenic alpha-amylase, beta-amylase, carboxypeptidase, catalase, chitinase, cutinase, cyclodextrin glycosyltransferase, deoxyribonuclease, esterase, galactanase, glucanase, alpha-galactosidase, beta-galactosidase, glucoamylase, alpha-glucosidase, beta-glucosidase, haloperoxidase, invertase, laccase, mannanase, mannosidase, oxidase, pectinolytic enzymes, peptidoglutaminase, peroxidase, phospholipase, phytase, polyphenoloxidase, proteolytic enzyme, ribonuclease, transglutaminase, and xylanase; especially a maltogenic alpha-amylase.

The compositions may be prepared in accordance with methods known in the art and may have any physical appearance such as liquid, paste or solid. For instance, the composition may be formulated using methods known to the art of formulating enzymes and/or pharmaceutical products, e.g., into coated or uncoated granules or micro-granules.

The lipolytic enzyme according to the invention and optionally any additional enzymes to be included in the composition may be stabilized in accordance with methods known in the art, e.g., by stabilizing the polypeptide in the composition by adding an antioxidant or reducing agent to limit oxidation of the polypeptide, or it may be stabilized by adding polymers such as PVP, PVA, PEG or other suitable polymers known to be beneficial to the stability of polypeptides in solid or liquid compositions.

When formulating the lipolytic enzyme according to the invention as a granulate or an agglomerated powder, the particles typically have a narrow particle size distribution with more than 95% (by weight) of the particles in the range from 25 to 500 micro-meter.

Granulates and agglomerated powders may be prepared by conventional methods, e.g., by spraying the lipolytic enzyme onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy. The composition is preferably in the form of a dry powder or a granulate, in particular a non-dusting granulate.

Hence, the invention also provides a granulate or a stabilized liquid comprising a lipolytic enzyme according to the invention.

Additional Enzymes

Optionally, one or more additional enzymes such as aminopeptidase, amylase, alpha-amylase, maltogenic alpha-amylase, beta-amylase, carboxypeptidase, catalase, chitinase, cutinase, cyclodextrin glycosyltransferase, deoxyribonuclease, esterase, galactanase, glucan 1,4-alpha-maltotetrahydrolase, glucanase, alpha-galactosidase, beta-galactosidase, glucoamylase, alpha-glucosidase, beta-glucosidase, haloperoxidase, invertase, laccase, mannanase, mannosidase, oxidase, pectinolytic enzymes, peptidoglutaminase, peroxidase, phospholipase, phytase, polyphenoloxidase, proteolytic enzyme, ribonuclease, transglutaminase, and/or xylanase may be used together with the lipolytic enzyme according to the present invention.

The glucoamylase for use in the present invention include glucoamylases having a sequence identity of at least 50%, at least 60%, at least 65%, at least 70%, at least 75%, at least 80%, at least 85%, at least 90%, at least 95%, at least 96%, at least 97%, at least 98%, or at least 99% to the amino acid sequence of the *A. niger* G1 or G2 glucoamylase (Boel et al. (1984), EMBO J. 3 (5), p. 1097-1102), the *A. awamori* glucoamylase disclosed in WO 84/02921, or the *A. oryzae* glucoamylase (Agric. Biol. Chem. (1991), 55 (4), p. 941-949).

The amylase may be fungal or bacterial, e.g., a maltogenic alpha-amylase from *B. stearothermophilus* or an alpha-amylase from *Bacillus*, e.g. *B. licheniformis* or *B. amyloliquefaciens*, a beta-amylase, e.g., from plant (e.g. soy bean) or from microbial sources (e.g., *Bacillus*), or a fungal alpha-amylase, e.g., from *A. oryzae*.

The maltogenic alpha-amylase may also be a maltogenic alpha-amylase as disclosed in, e.g., WO1999/043794; WO2006/032281; or WO2008/148845.

Suitable commercial maltogenic alpha-amylases include NOVAMYL, OPTICAKE 50 BG, and OPTICAKE 3D (available from Novozymes NS). Suitable commercial fungal alpha-amylase compositions include, e.g., BAKEZYME P 300 (available from DSM) and FUNGAMYL 2500 SG, FUNGAMYL 4000 BG, FUNGAMYL 800 L, FUNGAMYL ULTRA BG and FUNGAMYL ULTRA SG (available from Novozymes NS).

An anti-staling amylase may also be an amylase (glucan 1,4-alpha-maltotetrahydrolase (EC 3.2.1.60)) from, e.g., *Pseudomonas*, such as any of the amylases disclosed in WO1999/050399, WO2004/111217, or WO2005/003339.

The glucose oxidase may be a fungal glucose oxidase, in particular an *Aspergillus niger* glucose oxidase (such as GLUZYME®, available from Novozymes NS).

The hemicellulase may be a pentosanase, e.g., a xylanase which may be of microbial origin, e.g., derived from a bacterium or fungus, such as a strain of *Aspergillus*, in particular of *A. aculeatus*, *A. niger*, *A. awamori*, or *A. tubigensis*, from a strain of *Trichoderma*, e.g., *T. reesei*, or from a strain of *Humicola*, e.g., *H. insolens*.

Suitable commercially available xylanase preparations for use in the present invention include PANZEA BG, PENTOPAN MONO BG and PENTOPAN 500 BG (available from Novozymes NS), GRINDAMYL POWERBAKE (available from DuPont), and BAKEZYME BXP 5000 and BAKEZYME BXP 5001 (available from DSM).

The protease may be from *Bacillus*, e.g., *B. amyloliquefaciens* or from *Thermus aquaticus*.

Dough

In one aspect, the invention discloses a method for preparing dough or a baked product prepared from the dough which method comprises incorporating into the dough a lipolytic enzyme according to the invention.

In another aspect, the invention provides dough comprising flour, water, and an effective amount of a baking composition or a premix comprising the lipolytic enzyme according to the invention.

The present invention also relates to methods for preparing a dough or a baked product comprising incorporating into the dough an effective amount of a baking composition of the present invention which improves one or more properties of the dough or the baked product obtained from the dough relative to a dough or a baked product in which the lipolytic enzyme is not incorporated.

The phrase "incorporating into the dough" is defined herein as adding the baking composition according to the invention to the dough, to any ingredient from which the dough is to be made, and/or to any mixture of dough ingredients from which the dough is to be made. In other words, the baking composition of the invention may be added in any step of the dough preparation and may be added in one, two or more steps. The composition is added to the ingredients of dough that may be kneaded and baked to make the baked product using methods well known in the art.

The term "effective amount" is defined herein as an amount of baking composition according to the invention that is sufficient for providing a measurable effect on at least one property of interest of the dough and/or baked product.

The term "dough" is defined herein as a mixture of flour and other ingredients firm enough to knead or roll. In the context of the present invention, batters are encompassed in the term "dough".

The dough of the invention may comprise flour derived from any cereal grain or other sources, including wheat, emmer, spelt, einkorn, barley, rye, oat, corn, sorghum, rice, millet, amaranth, quinoa, and cassava.

The dough may also comprise other conventional dough ingredients, e.g., proteins, such as milk powder, gluten, and soy; eggs (either whole eggs, egg yolks, or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate, or calcium sulfate, and/or an emulsifier.

The dough may comprise fat (triglyceride) such as granulated fat or shortening.

The dough of the invention may be fresh, frozen or par-baked (pre-baked).

The dough of the invention is normally leavened dough or dough to be subjected to leavening.

The dough may be leavened in various ways, such as by adding chemical leavening agents, e.g., baking powder, sodium bicarbonate, or by adding a leaven (fermenting dough), but it is preferred to leaven the dough by adding a suitable yeast culture, such as a culture of *Saccharomyces cerevisiae* (baker's yeast), e.g., a commercially available strain of *S. cerevisiae*.

The lipolytic enzyme according to the invention may not change the baked product volume, in particular the bread volume, significantly; typically the volume may be increased or decreased by 0-5%.

The amount of lipolytic enzyme according to the invention may be between 0.01-100 mg enzyme protein per kg flour in the dough, in particular 0.05-50 mg enzyme protein per kg flour, in particular 0.1-25 mg enzyme protein per kg flour, in particular 0.1-15 mg enzyme protein per kg flour in the dough.

Emulsifiers

For some applications, an emulsifier is not needed; for some applications an emulsifier may be needed.

A suitable emulsifier for use in the present invention is preferably an emulsifier selected from the group consisting of diacetyl tartaric acid esters of monoglycerides (DATEM), sodium stearoyl lactylate (SSL), calcium stearoyl lactylate (CSL), ethoxylated mono- and diglycerides (EMG), distilled monoglycerides (DMG), polysorbates (PS), and succinylated monoglycerides (SMG).

In some applications, the lipolytic enzyme according to the present invention replaces all the emulsifier(s) usually present in the dough recipe.

Bread Improvers and Patisserie Mixes or Premixes

The lipolytic enzyme of the present invention may advantageously be part of a bread improver or a patisserie mix or a premix.

"Bread improvers" (also referred to as "dough conditioners" or "dough improvers" or "improving agents" or "flour treatment agents") are typically added to the dough in order to improve texture, structure, volume, flavour and freshness of the baked product as well as to improve machinability and stability of the dough.

Typically, a bread improver comprises or consists of: one or more enzyme(s) (such as e.g. amylases (alpha-amylases, beta-amylases, glucoamylases, raw starch degrading amylases), xylanases (hemicellulases), cellulases, pectinases, proteases, pectate lyases, oxidases (peroxidases, glucose oxidase, pyranose oxidases, hexose oxydases, L-amino acid oxidases, carbohydrate oxidases, sulfurhydryl oxidases), lipoxygenases, dehydrogenases, laccases, transglutaminases, acyltransferases, protein disulfide isomerases), one or more oxidizing or reducing agent(s) (such as, e.g., ascorbic acid, glutathione, cysteine), one or more emulsifier(s) (such as e.g. diacetyl tartaric acid esters of monoglycerides (DATEM), sodium stearoyl lactylate (SSL), calcium stearoyl lactylate (CSL), glycerol monostearate (GMS), rhamnolipids, lecithins, sucroesters, bile salts), one or more lipid material(s) (such as, e.g., butter, oil, shortening), one or more sugar(s), one or more flours or flour fraction(s), one or more vitamin(s) (such as, e.g., pantothenic acid and vitamin E), one or more gum(s), and/or one or more source(s) of fibre (such as, e.g., oat fibre).

Cake (patisserie) mixes typically comprise all the ingredients of a cake recipe with the exception of water, fat (oil, butter, margarine) and eggs. Eggs may be added in a cake (patisserie) mix in a powder form. Cake (patisserie) premixes are typically cake mixes where all or part of the flour and sugar has been removed.

Baked Product

The process of the invention may be used for any kind of baked product prepared from dough, particular of a soft character, either of a white, light or dark type. Examples are bread (in particular white, whole-meal or rye bread), typically in the form of loaves or rolls, bread, pita bread, tortillas, cakes, pancakes, biscuits, wafers, cookies, pie crusts, steamed bread, pizza and the like.

The present invention is further described by the following examples that should not be construed as limiting the scope of the invention.

EXAMPLES

Example 1

Cloning, Expression and Fermentation of the Lipolytic Enzyme According to the Invention Genomic DNA was extracted from a *Valsaria rubricosa* strain, using Fast DNA Spin for Soil Kit (Cat no. 6560-200 from MP Biochemicals) following the protocol from the supplier.

The *Valsaria rubricosa* strain was isolated from soil in Hunan, China, in 2002.

As known in the art, SEQ ID NO. 1 and 2 were amplified by PCR from the genomic DNA using a forward and reverse primer (SEQ ID NO. 3 and 4).

```
SEQ ID NO. 1 (signal peptide: 1-20):
MKSASILLRVAALLLPAVSALPLERRAISADLLATFSLFEQFAAAAYCPDNNDSPDTKLTCSVGNCPLVE

ADTTSTVTEFENSLETDVTGYVATDSTRELIVVAFRGSSSIRNWIADIDFPFTDTDLCDGCQAASGFWTS

WTEARTGVLAAVASAAAANPSYTVAVTGHSLGGAVAALAAGALRNAGYTVALYSFGAPRVGDETLSEYIT

AQAGGNYRITHLNDPVPKLPPLLLGYRHISPEYYISSGNNVTVTADDVEEYTGTINLSGNTGDLTFDTDA

HSWYFNEIGACDDGEALEWKKRGVEVQWV

SEQ ID NO. 2:
ATGAAGTCCGCTTCGATCTTACTCAGGGTAGCTGCCCTCCTCCTCCCTGCTGTATCTGCACTGCCACTTGAAAGAAG

AGGTATGGACGAACTATCCTAGCGATCAGTGTGTCTATTTTGCCTAACCTAGCAAAGCTATATCCGCGGATCTCCTG

GCAACCTTCAGCCTCTTCGAGCAGTTCGCAGCCGCAGCATATTGTCCGGATAACAACGACAGTCCCGACACCAAGCT

TACTTGCTCTGTCGGAAACTGCCCGCTTGTCGAAGCTGACACGACCAGCACGGTCACTGAATTCGAAAAGTACATCT

TACACGACCCCGTTCACCTACAGACAAAGTCCCAGCTAACGTCCACCTCTATCTCTGTCCCTTTAGCTCGCTCGAAA

CCGACGTCACTGGCTACGTCGCGACTGACAGCACACGAGAGCTCATCGTTGTGGCATTCCGCGGGAGTTCCTCGATC

CGGAACTGGATCGCCGACATCGACTTTCCCTTCACCGACACCGACCTCTGCGATGGCTGCCAGGCAGCCTCGGGCTT

CTGGACGTCCTGGACGGAGGCACGGACAGGGGTGCTGGCGGCGGTGGCGAGCGCTGCCGCGGCCAACCCGTCCTATA

CCGTTGCCGTGACGGGCCACAGCCTCGGCGGGGCCGTGGCCGCGCTGGCCGCTGGCGCCCTCCGGAACGCGGGCTAC

ACGGTCGCGCTATACAGCTTCGGAGCGCCTCGCGTGGGTGACGAGACCCTCAGCGAGTACATCACTGCGCAGGCGGG

TGGAAACTACCGCATCACGCACCTCAACGACCCAGTGCCGAAGCTGCCCCCGCTGCTCCTGGGGTATCGCCACATCA

GCCCGGAATACTACATCAGCAGCGGGAACAACGTGACCGTGACGGCGGATGACGTGGAGGAGTACACCGGCACGATC

AACCTGAGTGGGAACACGGGCGATCTGACGTTCGACACGGATGCGCACAGTTGGTACTTCAACGAGATCGGGGCATG

CGATGATGGTGAGGCTTTGGAGTGGAAGAAGCGGGGGGTAGAAGTTCAGTGGGTTTAA
```

SEQ ID NO: 3 (Primer):
5' ACACAACTGGGGATCCACCATGAAGTCCGCTTCGATCTTACTCAGG-3'

SEQ ID NO: 4 (Primer):
5' AGATCTCGAGAAGCTTAAACCCACTGAACTTCTACCCCCC-3'

The PCR product was purified using a GFX® PCR DNA and Gel Band Purification Kit (GE Healthcare, HiHerød, Denmark) according to manufacturer's instructions. The purified PCR product, corresponding to SEQ ID NO:2, was cloned into the expression vector pDAu109 (WO 2005/042735) previously linearized with Bam HI and Hind III, using an IN-FUSION™ PCR Cloning Kit (BD Biosciences, Palo Alto, Calif., USA) according to the manufacturer's instructions.

A 1 µl volume of the undiluted ligation mixture was used to transform Multi shot TOP 10 Chemical Competent Cells Part no. 44-0091 from Invitrogen. One colony was selected on a LB agar plate containing 100 µg of ampicillin per ml and cultivated overnight in 2 ml of LB medium supplemented with 100 µg of ampicillin per ml. Plasmid DNA was purified using a Jetquick Plasmid Miniprep Spin Kit (Genomed GmbH, Løhne, Germany) according to the manufacturer's instructions. The SEQ ID NO:2 sequence was verified by Sanger sequencing before heterologous expression. One plasmid (containing gene SEQ ID NO: 2), was selected for heterologous expression in *Aspergillus oryzae* host cells.

*A. oryzae* host cell is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene with the pyrG gene. Protoplasts of *Aspergillus oryzae* were prepared according to WO 95/002043.

One hundred µl of *Aspergillus oryzae* protoplasts were mixed with 1-2 µg of the *Aspergillus* expression vector with the cloned SEQ ID: 2 gene, and 250 µl of 60% PEG 4000 (Applichem, Darmstadt, Germany) (polyethylene glycol, molecular weight 4,000), 10 mM $CaCl_2$), and 10 mM Tris-HCl pH 7.5 were gently mixed. After 30 min of incubation at 37° C., 4 ml of top agar (temp. 40° C.) was added, and the protoplasts were spread onto COVE plates for selection. After incubation for 4-7 days at 37° C., spores of four transformants were inoculated into 0.5 ml of DAP-4C-01 medium in 96 deep well plates. After 4-5 days of cultivation at 30° C., the culture broths were analyzed by SDS-PAGE to identify the transformants producing the largest amount of recombinant protein from *Valsaria rubricosa*.

Spores of the best transformant with the SEQ ID NO:2 gene were spread on COVE plates containing 0.01% TRITON® X-100 in order to isolate single colonies. The spreading was repeated once more before preservation of the clones.

Fermentation for Purification

An *Aspergillus oryzae* transformant constructed as described above was fermented in 150 ml DAP-4C-01 medium in 500 ml fluted shake flasks incubated at 30° C. in a shaking platform incubator rotating at 150 RPM for 3-5 days and further used for assays as described below.

Medias Used

LB plates were composed of 10 g of Bacto-Tryptone, 5 g of yeast extract, 10 g of sodium chloride, 15 g of Bacto-agar, and deionized water to 1 liter.

LB medium was composed of 10 g of Bacto-Tryptone, 5 g of yeast extract, and 10 g of sodium chloride, and deionized water to 1 liter.

DAP-4C-1
11 g MgSO4,7H2O
1 g KH2PO4
2 g C6H8O7, H2O
20 g Dextrose
10 g Maltose
5.2 g K3PO4, H2O
0.5 g Yeast Extract
0.5 ml KU6 Trace metal sol. (AMG) (MSA-SUB-FS-0042)
Mix until completely dissolved
1 ml Dowfax 63N10 is added
Adjust volume with Milli-Q-water up to 1000 ml
CaCO3 tabl. of 0.5 g (add 1 tabl./200 ml)
Before inoculation, each shake flask of 150 ml is added 3.5 ml di-Ammoniumhydrogenphosphat (NH4)2HPO4 50%, and 5.0 ml Lactic acid 20%.
KU6 Trace Metal Sol. (AMG) (MSA-SUB-FS-0042)
6.8 g $ZnCl_2$
2.5 g $CuSO_4.5H2O$
0.13 g Nickel Chloride anhydrous
13.9 g $FeSO_4.7H2O$
8.45 g $MnSO_4.H2O$
3 g C6H8O7.H2O
Ion exchanged water up to 1000 ml COVE sucrose plates were composed of 342 g of sucrose, 20 g of agar powder, 20 ml of COVE salt solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, Triton X-100 (50 µl/500 ml) was added.

COVE salt solution was composed of 26 g of $MgSO_4.7H2O$, 26 g of KCL, 26 g of KH2PO4, 50 ml of COVE trace metal solution, and deionized water to 1 liter.

COVE trace metal solution was composed of 0.04 g of $Na_2B_4O_7.10H_2O$, 0.4 g of $CuSO_4.5H2O$, 1.2 g of $FeSO_4.7H2O$, 0.7 g of $MnSO_4.H2O$, 0.8 g of $Na_2MoO_4.2H2O$, 10 g of $ZnSO_4.7H2O$, and deionized water to 1 liter.

Features of SEQ ID NO:1:

The lipolytic enzyme (SEQ ID NO: 1) possesses a typical lipolytic enzyme box with catalytic triad featured in the pentapeptide: G-H-S-L-G (SEQ ID NO: 5).

The lipolytic enzyme (SEQ ID NO:1) according to the invention showed activity on tributyrin, MGDG (monogalactosyldiacylglycerol), DGDG (digalactosyldiacylglycerol), APE (N-acyl phosphatidyl ethanolamine), and ALPE (N-acyl lyso-phosphatidyl ethanolamine), which shows that the enzyme has lipase activity (tributyrin), phospholipase activity (APE/ALPE), and galactolipase activity (MGDG/DGDG).

pH Activity Profile of SEQ ID NO:1:

Purified SEQ ID NO:1 was diluted to 0.5, 0.125, 0.031 and 0.0078 mg enzyme protein/ml with 0.01% Triton X-100.

20 µl of the diluted enzyme samples were mixed with 40 µl pH buffer (0.1 M sodium acetate, 0.1 M sodium phosphate, 1 mM $CaCl_2$), adjusted to pH 2, 3, 4, 5, 6, 7, 8 and 9 using NaOH/HCl) and 40 μl olive oil substrate solution (12.5 mg/ml olive oil, 0.1% gum Arabic, 1.5 mM $CaCl_2$), homogenized by Ultra Turrax) in the wells of a 96 well microtiter plate.

After incubation at 37° C. for 30 min in an Eppendorf Thermomixer, the reaction was stopped by adding 10 μl stop reagent (1 M phosphoric acid, 10% Triton X-100) and mixing.

The concentration of liberated free fatty acids from the olive oil substrate was then quantified using a NEFA kit (Wako Diagnostics): 100 μl R1 kit reagent (Wako NEFA-HR (2) R1 SET, 434-91795) was mixed with 25 μl reaction volume, and absorbance at 546 nm was read on a Spectra-Max Plus plate reader. Then 50 μl R2 kit reagent (Wako NEFA-HR (2) R2 SET, 436-91995) was added, and after 20 min of incubation at room temperature (with shaking), absorbance at 546 nm was read again. From the difference between the two readings, concentration of free fatty acid was calculated using results with an oleic acid standard curve (1, 0.5, 0.25, 0.125, 0.0625, 0.03125 and 0 mM oleic acid). Lipase concentrations giving responses within the linear range were used to calculate activity at each pH. In Table A, activities relative to activity at pH 4 (pH optimum) are given.

TABLE A pH activity profile of SEQ ID NO: 1

| pH | Activity of SEQ ID NO: 1 relative to activity at pH 4 (%) |
|---|---|
| 2 | 0.8 |
| 3 | 9.4 |
| 4 | 100 |
| 5 | 60.6 |
| 6 | 4.7 |
| 7 | 0.3 |
| 8 | 0.0 |
| 9 | 0.1 |

Example 2

Bread samples were prepared according to a standard straight dough recipe by mixing the following ingredients (amount of dough was scaled up to fit requirement of baking trial):

| | |
|---|---|
| Wheat flour (Crousti flour, Dossche Mills, Deinze, Belgium) | 1000 g |
| Tap water | 570 g |
| Sucrose | 60 g |
| Yeast | 30 g |
| Rape seed oil | 20 g |
| Salt | 19 g |
| Calcium propionate | 5 g |
| Ascorbic acid | 40 ppm |
| Novamyl 10.000BG ™ (Novozymes A/S) | 40 ppm |
| Panzea Dual ™ (Novozymes A/S) | 25 ppm |

The following dough samples were made, and three bread samples were prepared from each dough. Soft'r Silk is a commercial DMG product from Puratos NV (Groot-Bijgaarden, Belgium) and used as benchmark for the effect of commercial DMG products. Soft'r Silk was dosed in relation to flour content.

TABLE 1

Enzyme dosage:

| Sample | Lipolytic enzyme dosage (mg EP/kg flour) |
|---|---|
| Control | — |
| 1% Soft'r Silk | — |
| SEQ ID NO: 1 | 0.4 |
| SEQ ID NO: 1 | 1.0 |

Dough was prepared by mixing ingredients in a spiral mixer (Diosna SP12, Dierks & Söhne, Osnabrück, Germany) for 2 min at slow speed (17 rpm) and 7 min at high speed (35 rpm). After mixing dough was evaluated before scaling (600 g). The scaled dough was left to rest for another 15 min before the dough was sheeted. The sheeted dough was placed in open 2200 mL steel pans (top measures: 260 mm(L)×125 mm(W)×80 mm(H)) and proofed for 90 min at 35° C., 86% relative humidity.

After proofing, the dough was baked in a deck oven (Wachtel Piccolo, Wachtel GmbH, Hilden, Germany) for 25 min at 230° C. Oven employed a short burst of steam at the start of the baking step. The baked bread was removed from the pans and left to cool at room temperature for 2 hours. Volume of the bread samples were determined using a Volscan Profiler 600 laser scanner (Stable Micro Systems, Surrey, UK). Subsequently, bread samples were packed with nitrogen in sealed plastic bags (PA/PE, 90 μm).

After two days of storage at room temperature, two slices were cut from the middle of each bread with an electric slicer (Graef Master M182 Slicer, Graef & Co GmbH, Arnsberg, Germany). Each slice was measured once using the C-cell instrument employing the C-Cell Image Analysis System Version 2.0 software (Calibre Control International Ltd, Warrington, UK).

The C-cell uses high definition imaging and controlled illumination of the sample to ensure optimum image quality. The whole slice is analyzed to provide 48 data values and 5 processed images showing particular features of the sample. Crumb whiteness can be evaluated using the parameter 'Slice brightness'. The brightness measurement is the average grey level of all of the pixels in the slice.

A finer crumb structure will give a higher 'Slice brightness' value.

TABLE 2

Bread volume data

| Sample | Lipolytic enzyme dosage (mg EP/kg flour) | Bread volume (mL/g) |
|---|---|---|
| Control | — | 5.45 |
| 1% Soft'r Silk | — | 5.18 |
| SEQ ID NO: 1 | 0.4 | 5.64 |
| SEQ ID NO: 1 | 1.0 | 5.28 |

TABLE 3

'Slice brightness' values for the tested samples.

| Sample | Lipolytic enzyme dosage (mg EP/kg flour) | C-cell parameter 'slice brightness' |
|---|---|---|
| Control | — | 144 |
| 1% Soft'r Silk | — | 148.6 |

TABLE 3-continued

'Slice brightness' values for the tested samples.

| Sample | Lipolytic enzyme dosage (mg EP/kg flour) | C-cell parameter 'slice brightness' |
|---|---|---|
| SEQ ID NO: 1 | 0.4 | 147.4 |
| SEQ ID NO: 1 | 1.0 | 149.7 |

It can be seen from Table 3 that by using the lipolytic enzyme according to the invention, the slice brightness is better than the control, and also better than 1% Soft'r Silk when using 1 mg lipolytic enzyme per kg flour.

Example 3

Bread samples were prepared identical to Example 2, except that King Midas Special flour (Ardent Mills Corp. Denver, Colo., US) was used instead of Crousti flour, and 600 g of water was added instead of the 570 g of water added in Example 2. Also, this trial did not include a Control, but only the benchmark with 1% Soft'r Silk.

TABLE 4

Enzyme dosage

| Sample | Lipolytic enzyme dosage (mg EP/kg flour) |
|---|---|
| 1% Soft'r Silk | — |
| SEQ ID NO: 1 | 0.4 |
| SEQ ID NO: 1 | 1.0 |

TABLE 5

Bread volume data

| Sample | Lipolytic enzyme dosage (mg EP/kg flour) | Bread volume (mL/g) |
|---|---|---|
| 1% Soft'r Silk | | 5.42 |
| SEQ ID NO: 1 | 0.4 | 5.27 |
| SEQ ID NO: 1 | 1.0 | 5.68 |

TABLE 6

'Slice brightness' values for the tested samples.

| Sample | Lipolytic enzyme dosage (mg EP/kg flour) | C-cell parameter 'slice brightness' |
|---|---|---|
| 1% Soft'r Silk | — | 151.1 |
| SEQ ID NO: 1 | 0.4 | 152.0 |
| SEQ ID NO: 1 | 1.0 | 153.6 |

It can be seen from Table 6 that by using the lipolytic enzyme according to the invention, the slice brightness is better than 1% Soft'r Silk (both at 0.4 and 1.0 mg lipolytic enzyme per kg flour).

Example 4

Construction of Variants

SEQ ID NO:6, SEQ ID NO:7, SEQ ID NO:8, and SEQ ID NO:9 were constructed in the following way: An alignment with SEQ ID NO:1 was made to the 100 most homologous lipases. Based on the alignment several positions were chosen, where SEQ ID NO:1 deviated from the average of the other lipases. A given position was mutated to the amino acids most commonly found in the other lipases. Four synthetic genes encoding the lipase variants were designed and the genes were expressed in *Aspergillus oryzae*.

```
SEQ ID NO: 6 (signal peptide: 1-20, 13 mutations as compared to
SEQ ID NO: 1 in mature sequence):
MKSASILLRVAALLLPAVSALPLERRAISADLLATFSLFEQFAAAAYCPNNNNSPDTKLTCSQGNCPLVEA

ATTSTVTEFENSLSTDVTGYVAVDSTRELIVVAFRGSSSIRNWIADIDFPFTDTDLCDGCQAASGFWQS

WTEARTGVTAAVASAAAQNPSYTVVVTGHSLGGAVAALAAGALRNQGYTVALYSFGAPRVGNETLSEY

ITAQAGGNYRITHLNDPVPKLPPLLLGYRHISPEYYISSGNNVTVTANDVEEYTGTINLSGNTGDLTFDTD

AHSWYFNEIGACDDGEALEWKKRGVEVQWV

SEQ ID NO: 7 (signal peptide: 1-20, 27 mutations as compared to
SEQ ID NO: 1 in mature sequence):
MKSASILLRVAALLLPAVSALPLERRAISADLLATFSLFEQFAAAAYCPNNNNSPGTKLTCSQGNCPLVEA

ATTNTVTEFENSLSTDVTGYVAVDSTNELIVVSFRGSSSIRNWIADIDFPFTDTDLCDGCQAASGFWQS

WTEARTTVTAAVAQAAAQNPSYQVVVTGHSLGGAIAALAAGALRNQGYTVDLYSFGAPRVGNETLSEYI

TNQAGGNYRITHLNDPVPKLPPLLMGYRHISPEYYISSGNNVTVTANDVQEYTGTINLQGNTGDLTFDID

AHSWYFNEIGACDDGEALEWKKRGVEVQWV

SEQ ID NO: 8 (signal peptide: 1-20, 41 mutations as compared to
SEQ ID NO: 1 in mature sequence):
MKSASILLRVAALLLPAVSALPLERRAISADLLATFQFFEQYAAAAYCPNNNNSPGTKLTCSQGNCPLVQ

AATTNTVYEFENSLSTDVTGYVAVDSTNKLIVVSFRGSSSIRNWIADIDFPFTDTDLCDGCQAASGFWQS

WLEARTTVTPAVAQARAQNPDYQVVVTGHSLGGAIAALAAGDLRNQGYTVDLYTFGAPRVGNETLSEY
```

-continued

```
ITNQAGGNYRITHWNDPVPKLPPLLMGYVHISPEYYISSGNNVTVTANDVQEYTGTINLQGNTGDLTFDI

DAHSWYFNEIGACDDGEALEWKKRGVEVQWV

SEQ ID NO: 9 (signal peptide: 1-20, 56 mutations as compared to
SEQ ID 1 in mature sequence):
MKSASILLRVAALLLPAVSALPLERRAISADLLDTFQFFEQYAAAAYCPNNNNSPGTKLTCSQGNCPLVQ

AADTNTVYEFENSLSTDVTGYVAVDHTNKLIVVSFRGSSSIRNWIADIDFPFTDTDLCDGCQAASGFWQ

SWLEARDTVTPAVYQARAQKPDYQVVVTGHSLGGAIAALAAGDLRNQGYTVDLYTFGAPRVGNSTLSE

YITNQPGGNYRVTHWNDPVPKLPPLLMGYVHISPEYYISSPNNVTVTANDVQVYEGVINLQGNEGDLTT

DIDAHSWYFNEIGACDDGEALEWKKRGVEVQWV
```

Example 5

Baking in American Toast with Various Lipolytic Enzymes

Bread was made as described in Example 2.

The lipolytic enzymes SEQ ID NO:6, and SEQ ID NO:7 were added to the dough in an amount of 0.4, 1, and 2 mg enzyme protein (EP)/kg flour. The lipolytic enzymes were produced as described in Example 4.

Bread volume and C-cell parameter 'slice brightness' were measured.

The following results were obtained—

TABLE 7

| Sample | Lipolytic enzyme dosage (mg EP/kg flour) | Bread volume (mL/g) | C-cell parameter 'slice brightness' |
|---|---|---|---|
| Control | | 5.08 | 138.2 |
| 1% Soft'r Silk | | 4.85 | 149.5 |
| SEQ ID NO: 6 | 0.4 | 4.24 | 145.7 |
| SEQ ID NO: 6 | 1 | 5.09 | 144.8 |
| SEQ ID NO: 6 | 2 | 5.11 | 139.8 |
| SEQ ID NO: 7 | 0.4 | 5.07 | 141.0 |
| SEQ ID NO: 7 | 1 | 5.23 | 147.5 |
| SEQ ID NO: 7 | 2 | 5.10 | 148.3 |

It can be seen from Table 7 that by using the lipolytic enzymes (SEQ ID NO:6 and SEQ ID NO:7) according to the invention, the slice brightness is higher than the control, and SEQ ID NO:7 is almost on par with 1% Soft'r Silk.

Example 6

Baking in American Toast with Various Lipolytic Enzymes

Bread was made as described in Example 2.

The lipolytic enzymes SEQ ID NO:8, and SEQ ID NO:9 were added to the dough in an amount of 0.4, 1, and 2 mg enzyme protein (EP)/kg flour (SEQ ID NO:8) and 0.4 mg enzyme protein (EP)/kg flour (SEQ ID NO:9). The lipolytic enzymes were produced as described in Example 4.

Bread volume, HunterLab L-value, and C-cell parameter 'slice brightness' were measured. HunterLab is a Colorimetric Spectrophotometric method using a light source to illuminate the sample, measuring the amount of light at different wavelengths. The light reflected by the sample passes to a grating which breaks it into its spectral components. Hunter L a b color space is a 3 dimensional rectangular color space, where L (lightness) axis: 0 is black and 100 is white. The numerical value correlates to what you see.

2 slices of each bread were used, and each slice was measured once using the HunterLab. The following results were obtained—

TABLE 8

| Sample | Lipolytic enzyme dosage (mg EP/kg flour) | Bread volume (mL/g) | HunterLab L-value | C-cell parameter 'slice brightness' |
|---|---|---|---|---|
| Control | | 5.17 | 79.6 | 134.7 |
| 1% Soft'r Silk | | 5.15 | 82.3 | 145.8 |
| SEQ ID NO: 8 | 0.4 | 5.36 | 80.2 | 140.6 |
| SEQ ID NO: 8 | 1 | 5.25 | 81.3 | 143.2 |
| SEQ ID NO: 8 | 2 | 5.24 | 80.3 | 140.6 |
| SEQ ID NO: 9 | 0.4 | 5.38 | 81.3 | 141.1 |

It can be seen from Table 8 that by using the lipolytic enzymes (SEQ ID NO:8 and SEQ ID NO:9) according to the invention, the slice brightness and/HunterLab L values are higher than the control. In conclusion, both SEQ ID NO:8, and SEQ ID NO:9 introduced crumb whiteness.

Example 7

Cookies with No Off-Flavor

Cookies were prepared using the ingredients of Table 9.

TABLE 9

| cookies ingredients | | | |
|---|---|---|---|
| Recipe (g) | A | B | C |
| Tegral Patacrout* (Puratos, Belgium) | 400 | 400 | 400 |
| Eggs | 40 | 40 | 40 |
| Butter | 160 | 160 | 160 |
| Lipopan 50 (Novozymes A/S) | | 0.04 | |
| SEQ ID NO: 1 (mg EP)** | | | 0.92 |

*Contains wheat flour, sugar, wheat gluten, raising agent (disodium diphosphate)
**0.92 mg (SEQ ID NO: 1 enzyme protein) was added per 400 g Tegral Patacrout Process:

The ingredients were blended in a Hobart mixer for 2 min at speed 1. The dough was packed in a plastic film and rested overnight at 25° C.

The next day, the dough was rolled out between 2 sheets of baking paper to a thickness of 2 mm. Pieces of 6.5 cm diameter were cut out.

The pieces of dough were baked in a Miwe Condo oven for 11 min at 180° C. No steam was added during baking.

Cookies Analysis:

The volatiles from a sample were determined using a HS-SPME-GC-MS technique. A Divinylbenzene/Carboxen/Polydimethylsiloxane (DVB/CAR/PDMS) fiber was used for the extraction of the volatile components.

The samples were firstly pre-heated for 10 min at 80° C. with a mixing speed of 250 rpm and then the extraction was carried out for 30 min at 80° C. under the same mixing speed.

The GC/MS analyses were performed with a gas chromatograph Agilent 5890A equipped with a mass spectrometer 5975C inert MSD with Triple-Axis Detector and an autosampler Gerstel MPS configured for automated SPME analysis. Separation of the analytes was performed on a RESTEK Stabilwax capillary column, 30 m×0.25 mm×0.50 μm film thickness. The column oven was programmed as follows: initial temperature 80° C. for 10 min, ramped at 16° C./min to 220° C., which was held at 220° C. for 8 min. Helium was used as carrier gas with a constant flow-rate of 1 mL/min. The volatile compounds were identified by comparison with the mass spectra of the NIST MS Search 2.0 library.

The volatile components: butanoic, hexanoic, octanoic, and decanoic acids, are responsible for strong off-flavor. Table 8 shows the concentrations of butanoic, hexanoic, octanoic, and decanoic acids.

TABLE 10

Relative concentration (peak area) of volatile components identified in the cookie samples

| | A | B | C |
|---|---|---|---|
| Butanoic acid | 151,000,000 | 1191,000,000 | 243,000,000 |
| Hexanoic acid | 398,000,000 | 2050,000,000 | 580,000,000 |
| Octanoic acid | 210,000,000 | 2650,000,000 | 200,000,000 |
| Decanoic acid | Not detectable | 989,000,000 | 28,100,000 |

Table 10 shows that the cookies made with a commercial lipase have a much higher content of butanoic, hexanoic, octanoic, and decanoic acids compared with the cookies made with the lipolytic enzyme according to the invention.

Additionally, the trained baking personnel could not perceive any off-flavor in the cookies made with the enzyme according to the invention, but they could perceive a strong off-flavor in the cookies made with the commercial lipase.

Example 8

Brioches with No Off-Flavor

Brioches were prepared using the ingredients of Table 11.

TABLE 11 brioche ingredients

| Recipe (g) | D | E | F |
|---|---|---|---|
| Flour (Crousti flour, Dossche Mills, Deinze, Belgium) at 7° C. | 1500 | 1500 | 1500 |
| Water at 4° C. | 450 | 450 | 450 |
| Yeast (Bruggeman Brown instant yeast) | 30 | 30 | 30 |
| Salt | 24 | 24 | 24 |
| Sugar S1 | 270 | 270 | 270 |
| Butter | 225 | 225 | 225 |
| Eggs | 300 | 300 | 300 |
| AML Brioche (Puratos, Belgium)* | 30 | 30 | 30 |
| Lipopan 50 (Novozymes A/S) | | 1.15 | |
| SEQ ID NO: 1 (mg EP)** | | | 3.47 |

*Contains wheat flour, hydrolysed wheat gluten, antioxidant (ascorbic acid) & enzymes.
**3.47 mg (SEQ ID NO: 1 enzyme protein) was added per 1500 g flour Process:

The following process was used:

Mix the different ingredients in a Diosna SP24 for 6 min at slow speed and for 11 min at fast speed (only add the fat after 4 min fast mixing). The final dough temperature is around 27° C.

Perform a bulk fermentation for 10 min at ambient temperature at 25° C.

Scale to 500 g dough.

Mould manually the bread.

Perform an intermediate proofing time of 20 min at 25° C.

Mould on a Jac Unic with R4.5 and L16.

Proof for 165 min at 28° C. and 95% RH in a Koma fermentation room.

Bake for 30 minutes at 200° C. in a Miwe Condo oven.

Let the brioches cool for 90 minutes and pack the bread in plastic bags.

Brioches Analysis:

The analysis of the volatiles (same volatiles as described in Example 4) was performed on the brioches.

Table 12 shows the concentrations of butanoic, hexanoic, octanoic, and decanoic acids.

TABLE 12

Relative concentration (peak area) of volatile components identified in the brioche samples

| | D | E | F |
|---|---|---|---|
| Butanoic acid | 69,700,000 | 74,800,000 | 65,400,000 |
| Hexanoic acid | 101,000,000 | 513,000,000 | 187,000,000 |
| Octanoic acid | 93,800,000 | 625,000,000 | 151,000,000 |
| Decanoic acid | Not detectable | 140,000,000 | Not detectable |

Table 12 shows that the brioches made with a commercial lipase have a higher content of butanoic, hexanoic, octanoic, and decanoic acids compared with the brioches made with the lipolytic enzyme according to the invention.

Additionally, the trained baking personnel could not perceive any off-flavor in the brioches made with the enzyme according to the invention, but they could perceive a strong off-flavor in the brioches made with the commercial lipase.

It is to be noted that the brioches made with the enzymes (E & F) gave a finer crumb than the brioches with butter alone (judged by the trained baking personnel).

Example 9

Bread Produced with the Enzyme According to the Invention

Bread was prepared using the ingredients of Table 13.

TABLE 13

Bread ingredients

| Recipe (g) | G | H | I | J |
|---|---|---|---|---|
| Flour (Crousti flour, Dossche Mills, Deinze, Belgium) at 7° C. | 1500 | 1500 | 1500 | 1500 |
| Water at 12° C. | 810 | 810 | 810 | 810 |
| Fresh Yeast | 45 | 45 | 45 | 45 |
| Salt | 28.5 | 28.5 | 28.5 | 28.5 |
| Sugar (sucrose) | 90 | 90 | 90 | 90 |
| Rapeseed oil | 30 | 30 | 30 | 30 |

TABLE 13-continued

Bread ingredients

| Recipe (g) | G | H | I | J |
|---|---|---|---|---|
| Calcium propionate | 7.5 | 7.5 | 7.5 | 7.5 |
| Bread Improver (Puratos, Belgium)* | 15 | 15 | 15 | 15 |
| SEQ ID NO: 1 (mg EP)** | | | 3.47 | |
| Bakezyme L80000 (DSM, the Netherlands) (mg) | | | | 4.2 |
| Amanolipase DF15 (Amano, Japan) (mg) | | 22.5 | | |

*Contains wheat flour, antioxidant (ascorbic acid) & enzymes (amylase, xyanase).
**3.47 mg (SEQ ID NO: 1 enzyme protein) was added per 1500 g flour Process:

The following process was used:
Mix the different ingredients in a Diosna SP24 for 2 min at slow speed and for 7 min at fast speed. The final dough temperature is around 26° C.
Perform a bulk fermentation for 5 min at ambient temperature at 25° C.
Scale 600 g dough.
Mould manually the bread.
Perform an intermediate proofing time of 15 min at 25° C.
Mould on a Jac Unic with R4.5 and L15.
Proof for 110 min at 35° C. and 95% RH in a Koma fermentation room.
Bake for 25 minutes at 220/230° C. (above/under) in a Miwe Condo oven.
Let the bread cool for 120 minutes and pack the bread in plastic bags.

Bread Texture Measurement:

For the hardness measurement, a TA.XT from Stable Micro Systems (TA.XT plus) was used. 10 repetitions (different bread) were measured with a probe of diameter 25 mm with a speed of 2 mm/s and compressed with a force of 25% of total height into the bread crumb. Hardness measurements are shown in the table 14.

TABLE 14

Hardness measurements on bread samples, measured at day 2

| | G | H | I | J |
|---|---|---|---|---|
| Hardness (average) (g) | 211 | 161 | 200 | 195 |
| stdev | 21 | 14 | 12 | 15 |

The results show that the bread made with the enzyme according to the invention is significantly softer than the reference. The breads made with commercial lipases are similar in softness to the reference.

The invention claimed is:

1. A method for preparing a baked product, comprising
   (a) adding a polypeptide having lipolytic activity to a dough prior to baking, wherein the polypeptide comprises an amino acid sequence having at least 80% sequence identity to the sequence of amino acids 21 to 309 of SEQ ID NO: 1; and
   (b) baking the dough to produce the baked product.

2. The method of claim 1, wherein the polypeptide comprises a lipolytic enzyme catalytic segment of the amino acid sequence G-H-S-L-G (SEQ ID NO: 5).

3. The method of claim 2, wherein the polypeptide comprises an amino acid sequence having at least 85% sequence identity to the sequence of amino acids 21 to 309 of SEQ ID NO: 1.

4. The method of claim 2, wherein the polypeptide comprises an amino acid sequence having at least 90% sequence identity to the sequence of amino acids 21 to 309 of SEQ ID NO: 1.

5. The method of claim 2, wherein the polypeptide comprises an amino acid sequence having at least 95% sequence identity to the sequence of amino acids 21 to 309 of SEQ ID NO: 1.

6. The method of claim 2, wherein the polypeptide comprises an amino acid sequence having at least 97% sequence identity to the sequence of amino acids 21 to 309 of SEQ ID NO: 1.

7. The method of claim 2, wherein the polypeptide comprises the amino acid sequence of amino acids 21 to 309 of SEQ ID NO: 1.

8. The method of claim 2, wherein the polypeptide comprises the amino acid sequence of amino acids 21 to 309 of SEQ ID NO: 6.

9. The method of claim 2, wherein the polypeptide comprises the amino acid sequence of amino acids 21 to 309 of SEQ ID NO: 7.

10. The method of claim 2, wherein the polypeptide comprises the amino acid sequence of amino acids 21 to 309 of SEQ ID NO: 8.

11. The method of claim 2, wherein the polypeptide comprises the amino acid sequence of amino acids 21 to 309 of SEQ ID NO: 9.

12. The method of claim 2, wherein the polypeptide is encoded by a polynucleotide that hybridizes under medium stringency conditions with the full-length complement of the nucleotide sequence of SEQ ID NO: 2, wherein the medium stringency conditions are defined as prehybridization and hybridization at 42° C. in 5×SSPE, 0.3% SDS, 200 micrograms/ml sheared and denatured salmon sperm DNA, and 35% formamide, for 12 to 24 hours, followed by washing three times each for 15 minutes using 2×SSC, 0.2% SDS at 55° C.

13. The method of claim 2, wherein the polypeptide is a fragment of the sequence of amino acids 21 to 309 of SEQ ID NO: 1, wherein the fragment has lipolytic enzyme activity.

14. The method of claim 1, wherein the polypeptide has lipase and phospholipase activity.

15. The method of claim 1, wherein the amount of the polypeptide added is between 0.01 and 100 mg of the polypeptide per kg flour in the dough.

16. The method of claim 1, wherein the amount of the polypeptide added is between 0.05 and 50 mg of the polypeptide per kg flour in the dough.

17. The method of claim 1, wherein the amount of the polypeptide added is between 0.1 and 25 mg of the polypeptide per kg flour in the dough.

18. The method of claim 1, wherein the amount of the polypeptide added is between 0.1 and 15 mg of the polypeptide per kg flour in the dough.

19. The method of claim 1, wherein the baked product has an improved crumb property compared to a baked product prepared without the polypeptide.

20. The method of claim 19, wherein the improved crumb property is improved whiteness of the crumb of the baked product, improved crumb structure of the baked product, improved crumb softness of the baked product, improved flavor of the baked product, and/or improved anti-staling properties of the baked product.

\* \* \* \* \*

SEQUENCE LISTING

```
<160> NUMBER OF SEQ ID NOS: 9

<210> SEQ ID NO 1
<211> LENGTH: 309
<212> TYPE: PRT
<213> ORGANISM: Valsaria rubricosa

<400> SEQUENCE: 1

Met Lys Ser Ala Ser Ile Leu Leu Arg Val Ala Ala Leu Leu Leu Pro
1               5                   10                  15

Ala Val Ser Ala Leu Pro Leu Glu Arg Arg Ala Ile Ser Ala Asp Leu
            20                  25                  30

Leu Ala Thr Phe Ser Leu Phe Glu Gln Phe Ala Ala Ala Ala Tyr Cys
        35                  40                  45

Pro Asp Asn Asn Asp Ser Pro Asp Thr Lys Leu Thr Cys Ser Val Gly
    50                  55                  60

Asn Cys Pro Leu Val Glu Ala Asp Thr Thr Ser Thr Val Thr Glu Phe
65                  70                  75                  80

Glu Asn Ser Leu Glu Thr Asp Val Thr Gly Tyr Val Ala Thr Asp Ser
                85                  90                  95

Thr Arg Glu Leu Ile Val Val Ala Phe Arg Gly Ser Ser Ser Ile Arg
            100                 105                 110

Asn Trp Ile Ala Asp Ile Asp Phe Pro Phe Thr Asp Thr Asp Leu Cys
        115                 120                 125

Asp Gly Cys Gln Ala Ala Ser Gly Phe Trp Thr Ser Trp Thr Glu Ala
    130                 135                 140

Arg Thr Gly Val Leu Ala Ala Val Ala Ser Ala Ala Ala Ala Asn Pro
145                 150                 155                 160

Ser Tyr Thr Val Ala Val Thr Gly His Ser Leu Gly Gly Ala Val Ala
                165                 170                 175

Ala Leu Ala Ala Gly Ala Leu Arg Asn Ala Gly Tyr Thr Val Ala Leu
            180                 185                 190
```

Tyr Ser Phe Gly Ala Pro Arg Val Gly Asp Glu Thr Leu Ser Glu Tyr
            195                 200                 205

Ile Thr Ala Gln Ala Gly Gly Asn Tyr Arg Ile Thr His Leu Asn Asp
        210                 215                 220

Pro Val Pro Lys Leu Pro Pro Leu Leu Leu Gly Tyr Arg His Ile Ser
225                 230                 235                 240

Pro Glu Tyr Tyr Ile Ser Ser Gly Asn Asn Val Thr Val Thr Ala Asp
                245                 250                 255

Asp Val Glu Glu Tyr Thr Gly Thr Ile Asn Leu Ser Gly Asn Thr Gly
            260                 265                 270

Asp Leu Thr Phe Asp Thr Asp Ala His Ser Trp Tyr Phe Asn Glu Ile
        275                 280                 285

Gly Ala Cys Asp Asp Gly Glu Ala Leu Glu Trp Lys Lys Arg Gly Val
    290                 295                 300

Glu Val Gln Trp Val
305

<210> SEQ ID NO 2
<211> LENGTH: 1059
<212> TYPE: DNA
<213> ORGANISM: Valsaria rubricosa

<400> SEQUENCE: 2

| | | | | | |
|---|---|---|---|---|---|
| atgaagtccg | cttcgatctt | actcagggta | gctgccctcc | tcctccctgc | tgtatctgca | 60 |
| ctgccacttg | aaagaagagg | tatggacgaa | ctatcctagc | gatcagtgtg | tctattttgc | 120 |
| ctaacctagc | aaagctatat | ccgcggatct | cctggcaacc | ttcagcctct | tcgagcagtt | 180 |
| cgcagccgca | gcatattgtc | cggataacaa | cgacagtccc | gacaccaagc | ttacttgctc | 240 |
| tgtcggaaac | tgcccgcttg | tcgaagctga | cacgaccagc | acggtcactg | aattcgaaaa | 300 |
| gtacatctta | cacgaccccg | ttcacctaca | gacaaagtcc | cagctaacgt | ccacctctat | 360 |
| ctctgtccct | ttagctcgct | cgaaaccgac | gtcactggct | acgtcgcgac | tgacagcaca | 420 |
| cgagagctca | tcgttgtggc | attccgcggg | agttcctcga | tccggaactg | gatcgccgac | 480 |
| atcgactttc | ccttcaccga | caccgacctc | tgccatggct | gccaggcagc | tcgggcttc | 540 |
| tggacgtcct | ggacggaggc | acggacaggg | gtgctggcgg | cggtggcgag | cgctgccgcg | 600 |
| gccaacccgt | cctataccgt | tgccgtgacg | ggccacagcc | tcggcggggc | cgtgccgcg | 660 |
| ctggccgctg | gcgccctccg | gaacgcgggc | tacacggtcg | cgctatacag | cttcggagcg | 720 |
| cctcgcgtgg | gtgacgagac | cctcagcgag | tacatcactg | cgcaggcggg | tggaaactac | 780 |
| cgcatcacgc | acctcaacga | cccagtgccg | aagctgcccc | cgctgctcct | ggggtatcgc | 840 |
| cacatcagcc | cggaatacta | catcagcagc | gggaacaacg | tgaccgtgac | ggcggatgac | 900 |
| gtggaggagt | acaccggcac | gatcaacctg | agtgggaaca | cgggcgatct | gacgttcgac | 960 |
| acggatgcgc | acagttggta | cttcaacgag | atcggggcat | gcgatgatgg | tgaggctttg | 1020 |
| gagtggaaga | agcgggggt | agaagttcag | tgggtttaa | | | 1059 |

<210> SEQ ID NO 3
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 3
acacaactgg ggatccacca tgaagtccgc ttcgatctta ctcagg 46

<210> SEQ ID NO 4
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 4
agatctcgag aagcttaaac ccactgaact tctacccccc    40

<210> SEQ ID NO 5
<211> LENGTH: 5
<212> TYPE: PRT
<213> ORGANISM: Artificial Sequence
<220> FEATURE:
<223> OTHER INFORMATION: Catalytic segment

<400> SEQUENCE: 5

Gly His Ser Leu Gly
1               5

<210> SEQ ID NO 6
<211> LENGTH: 309
<212> TYPE: PRT
<213> ORGANISM: Artificial Sequence
<220> FEATURE:
<223> OTHER INFORMATION: Lipase variant encoded by synthetic gene

<400> SEQUENCE: 6

Met Lys Ser Ala Ser Ile Leu Leu Arg Val Ala Ala Leu Leu Leu Pro
1               5                   10                  15

Ala Val Ser Ala Leu Pro Leu Glu Arg Arg Ala Ile Ser Ala Asp Leu
            20                  25                  30

Leu Ala Thr Phe Ser Leu Phe Glu Gln Phe Ala Ala Ala Ala Tyr Cys
        35                  40                  45

Pro Asn Asn Asn Ser Pro Asp Thr Lys Leu Thr Cys Ser Gln Gly
    50                  55                  60

Asn Cys Pro Leu Val Glu Ala Ala Thr Thr Ser Thr Val Thr Glu Phe
65                  70                  75                  80

Glu Asn Ser Leu Ser Thr Asp Val Thr Gly Tyr Val Ala Val Asp Ser
                85                  90                  95

Thr Arg Glu Leu Ile Val Val Ala Phe Arg Gly Ser Ser Ile Arg
            100                 105                 110

Asn Trp Ile Ala Asp Ile Asp Phe Pro Phe Thr Asp Thr Asp Leu Cys
        115                 120                 125

Asp Gly Cys Gln Ala Ala Ser Gly Phe Trp Gln Ser Trp Thr Glu Ala
    130                 135                 140

Arg Thr Gly Val Thr Ala Ala Val Ala Ser Ala Ala Ala Gln Asn Pro
145                 150                 155                 160

Ser Tyr Thr Val Val Thr Gly His Ser Leu Gly Gly Ala Val Ala
                165                 170                 175

Ala Leu Ala Ala Gly Ala Leu Arg Asn Gln Gly Tyr Thr Val Ala Leu
            180                 185                 190

Tyr Ser Phe Gly Ala Pro Arg Val Gly Asn Glu Thr Leu Ser Glu Tyr
        195                 200                 205

Ile Thr Ala Gln Ala Gly Gly Asn Tyr Arg Ile Thr His Leu Asn Asp
    210                 215                 220

Pro Val Pro Lys Leu Pro Pro Leu Leu Leu Gly Tyr Arg His Ile Ser

```
225                 230                 235                 240

Pro Glu Tyr Tyr Ile Ser Ser Gly Asn Asn Val Thr Val Thr Ala Asn
                245                 250                 255

Asp Val Glu Glu Tyr Thr Gly Thr Ile Asn Leu Ser Gly Asn Thr Gly
                260                 265                 270

Asp Leu Thr Phe Asp Thr Asp Ala His Ser Trp Tyr Phe Asn Glu Ile
                275                 280                 285

Gly Ala Cys Asp Asp Gly Glu Ala Leu Glu Trp Lys Lys Arg Gly Val
                290                 295                 300

Glu Val Gln Trp Val
305

<210> SEQ ID NO 7
<211> LENGTH: 309
<212> TYPE: PRT
<213> ORGANISM: Artificial Sequence
<220> FEATURE:
<223> OTHER INFORMATION: Lipase variant encoded by synthetic gene

<400> SEQUENCE: 7

Met Lys Ser Ala Ser Ile Leu Leu Arg Val Ala Ala Leu Leu Leu Pro
1               5                   10                  15

Ala Val Ser Ala Leu Pro Leu Glu Arg Arg Ala Ile Ser Ala Asp Leu
                20                  25                  30

Leu Ala Thr Phe Ser Leu Phe Glu Gln Phe Ala Ala Ala Ala Tyr Cys
                35                  40                  45

Pro Asn Asn Asn Asn Ser Pro Gly Thr Lys Leu Thr Cys Ser Gln Gly
                50                  55                  60

Asn Cys Pro Leu Val Glu Ala Ala Thr Thr Asn Thr Val Thr Glu Phe
65                  70                  75                  80

Glu Asn Ser Leu Ser Thr Asp Val Thr Gly Tyr Val Ala Val Asp Ser
                85                  90                  95

Thr Asn Glu Leu Ile Val Val Ser Phe Arg Gly Ser Ser Ser Ile Arg
                100                 105                 110

Asn Trp Ile Ala Asp Ile Asp Phe Pro Phe Thr Asp Thr Asp Leu Cys
                115                 120                 125

Asp Gly Cys Gln Ala Ala Ser Gly Phe Trp Gln Ser Trp Thr Glu Ala
                130                 135                 140

Arg Thr Thr Val Thr Ala Ala Val Ala Gln Ala Ala Ala Gln Asn Pro
145                 150                 155                 160

Ser Tyr Gln Val Val Thr Gly His Ser Leu Gly Gly Ala Ile Ala
                165                 170                 175

Ala Leu Ala Ala Gly Ala Leu Arg Asn Gln Gly Tyr Thr Val Asp Leu
                180                 185                 190

Tyr Ser Phe Gly Ala Pro Arg Val Gly Asn Glu Thr Leu Ser Glu Tyr
                195                 200                 205

Ile Thr Asn Gln Ala Gly Gly Asn Tyr Arg Ile Thr His Leu Asn Asp
                210                 215                 220

Pro Val Pro Lys Leu Pro Pro Leu Leu Met Gly Tyr Arg His Ile Ser
225                 230                 235                 240

Pro Glu Tyr Tyr Ile Ser Ser Gly Asn Asn Val Thr Val Thr Ala Asn
                245                 250                 255

Asp Val Gln Glu Tyr Thr Gly Thr Ile Asn Leu Gln Gly Asn Thr Gly
                260                 265                 270

Asp Leu Thr Phe Asp Ile Asp Ala His Ser Trp Tyr Phe Asn Glu Ile
```

```
                275                 280                 285
Gly Ala Cys Asp Asp Gly Glu Ala Leu Glu Trp Lys Lys Arg Gly Val
            290                 295                 300

Glu Val Gln Trp Val
305

<210> SEQ ID NO 8
<211> LENGTH: 309
<212> TYPE: PRT
<213> ORGANISM: Artificial Sequence
<220> FEATURE:
<223> OTHER INFORMATION: Lipase variant encoded by synthetic gene

<400> SEQUENCE: 8

Met Lys Ser Ala Ser Ile Leu Leu Arg Val Ala Ala Leu Leu Leu Pro
1               5                   10                  15

Ala Val Ser Ala Leu Pro Leu Glu Arg Arg Ala Ile Ser Ala Asp Leu
            20                  25                  30

Leu Ala Thr Phe Gln Phe Phe Glu Gln Tyr Ala Ala Ala Ala Tyr Cys
        35                  40                  45

Pro Asn Asn Asn Ser Pro Gly Thr Lys Leu Thr Cys Ser Gln Gly
50                  55                  60

Asn Cys Pro Leu Val Gln Ala Ala Thr Thr Asn Thr Val Tyr Glu Phe
65                  70                  75                  80

Glu Asn Ser Leu Ser Thr Asp Val Thr Gly Tyr Val Ala Val Asp Ser
                85                  90                  95

Thr Asn Lys Leu Ile Val Val Ser Phe Arg Gly Ser Ser Ser Ile Arg
            100                 105                 110

Asn Trp Ile Ala Asp Ile Asp Phe Pro Phe Thr Asp Thr Asp Leu Cys
        115                 120                 125

Asp Gly Cys Gln Ala Ala Ser Gly Phe Trp Gln Ser Trp Leu Glu Ala
130                 135                 140

Arg Thr Thr Val Thr Pro Ala Val Ala Gln Ala Arg Ala Gln Asn Pro
145                 150                 155                 160

Asp Tyr Gln Val Val Thr Gly His Ser Leu Gly Gly Ala Ile Ala
                165                 170                 175

Ala Leu Ala Ala Gly Asp Leu Arg Asn Gln Gly Tyr Thr Val Asp Leu
            180                 185                 190

Tyr Thr Phe Gly Ala Pro Arg Val Gly Asn Glu Thr Leu Ser Glu Tyr
        195                 200                 205

Ile Thr Asn Gln Ala Gly Gly Asn Tyr Arg Ile Thr His Trp Asn Asp
210                 215                 220

Pro Val Pro Lys Leu Pro Pro Leu Leu Met Gly Tyr Val His Ile Ser
225                 230                 235                 240

Pro Glu Tyr Tyr Ile Ser Ser Gly Asn Asn Val Thr Val Thr Ala Asn
                245                 250                 255

Asp Val Gln Glu Tyr Thr Gly Thr Ile Asn Leu Gln Gly Asn Thr Gly
            260                 265                 270

Asp Leu Thr Phe Asp Ile Asp Ala His Ser Trp Tyr Phe Asn Glu Ile
        275                 280                 285

Gly Ala Cys Asp Asp Gly Glu Ala Leu Glu Trp Lys Lys Arg Gly Val
            290                 295                 300

Glu Val Gln Trp Val
305
```

```
<210> SEQ ID NO 9
<211> LENGTH: 309
<212> TYPE: PRT
<213> ORGANISM: Artificial Sequence
<220> FEATURE:
<223> OTHER INFORMATION: Lipase variant encoded by synthetic gene

<400> SEQUENCE: 9

Met Lys Ser Ala Ser Ile Leu Leu Arg Val Ala Ala Leu Leu Leu Pro
1               5                   10                  15

Ala Val Ser Ala Leu Pro Leu Glu Arg Arg Ala Ile Ser Ala Asp Leu
            20                  25                  30

Leu Asp Thr Phe Gln Phe Phe Glu Gln Tyr Ala Ala Ala Tyr Cys
        35                  40                  45

Pro Asn Asn Asn Asn Ser Pro Gly Thr Lys Leu Thr Cys Ser Gln Gly
    50                  55                  60

Asn Cys Pro Leu Val Gln Ala Ala Asp Thr Asn Thr Val Tyr Glu Phe
65                  70                  75                  80

Glu Asn Ser Leu Ser Thr Asp Val Thr Gly Tyr Val Ala Val Asp His
                85                  90                  95

Thr Asn Lys Leu Ile Val Val Ser Phe Arg Gly Ser Ser Ile Arg
            100                 105                 110

Asn Trp Ile Ala Asp Ile Asp Phe Pro Phe Thr Asp Thr Asp Leu Cys
        115                 120                 125

Asp Gly Cys Gln Ala Ala Ser Gly Phe Trp Gln Ser Trp Leu Glu Ala
    130                 135                 140

Arg Asp Thr Val Thr Pro Ala Val Tyr Gln Ala Arg Ala Gln Lys Pro
145                 150                 155                 160

Asp Tyr Gln Val Val Thr Gly His Ser Leu Gly Gly Ala Ile Ala
                165                 170                 175

Ala Leu Ala Ala Gly Asp Leu Arg Asn Gln Gly Tyr Thr Val Asp Leu
            180                 185                 190

Tyr Thr Phe Gly Ala Pro Arg Val Gly Asn Ser Thr Leu Ser Glu Tyr
        195                 200                 205

Ile Thr Asn Gln Pro Gly Gly Asn Tyr Arg Val Thr His Trp Asn Asp
    210                 215                 220

Pro Val Pro Lys Leu Pro Pro Leu Leu Met Gly Tyr Val His Ile Ser
225                 230                 235                 240

Pro Glu Tyr Tyr Ile Ser Ser Pro Asn Asn Val Thr Val Thr Ala Asn
                245                 250                 255

Asp Val Gln Val Tyr Glu Gly Val Ile Asn Leu Gln Gly Asn Glu Gly
            260                 265                 270

Asp Leu Thr Thr Asp Ile Asp Ala His Ser Trp Tyr Phe Asn Glu Ile
        275                 280                 285

Gly Ala Cys Asp Asp Gly Glu Ala Leu Glu Trp Lys Lys Arg Gly Val
    290                 295                 300

Glu Val Gln Trp Val
305
```